(12) United States Patent
Bassin

(10) Patent No.: US 8,899,231 B2
(45) Date of Patent: Dec. 2, 2014

(54) METHODS FOR PROVIDING EXPIRATORY PRESSURE RELIEF IN POSITIVE AIRWAY PRESSURE THERAPY

(75) Inventor: David John Bassin, Coogee (AU)

(73) Assignee: ResMed Limited (AU)

( * ) Notice: Subject to any disclaimer, the term of this patent is extended or adjusted under 35 U.S.C. 154(b) by 854 days.

(21) Appl. No.: 12/961,169

(22) Filed: Dec. 6, 2010

(65) Prior Publication Data

US 2011/0092841 A1    Apr. 21, 2011

Related U.S. Application Data

(63) Continuation of application No. 10/596,813, filed as application No. PCT/AU2005/000006 on Jan. 7, 2005, now Pat. No. 7,866,318.

(30) Foreign Application Priority Data

Jan. 7, 2004 (AU) .................................. 2004900046

(51) Int. Cl.
| | |
|---|---|
| *A61M 11/00* | (2006.01) |
| *A61M 16/00* | (2006.01) |
| *A61M 16/06* | (2006.01) |

(52) U.S. Cl.
CPC ....... *A61M 16/00* (2013.01); *A61M 2016/0024* (2013.01); *A61M 16/0069* (2013.01); *A61M 16/06* (2013.01)
USPC ................... 128/204.23; 128/204.21

(58) Field of Classification Search
USPC .......................... 128/200.24, 202.22, 204.18, 128/204.21–204.23
See application file for complete search history.

(56) References Cited

U.S. PATENT DOCUMENTS

| | | | |
|---|---|---|---|
| 3,961,627 | A | 6/1976 | Ernst et al. |
| 4,944,310 | A | 7/1990 | Sullivan |
| 5,044,362 | A | 9/1991 | Younes |
| 5,107,830 | A | 4/1992 | Younes |
| 5,148,802 | A | 9/1992 | Sanders |
| 5,535,738 | A | 7/1996 | Estes |
| 5,540,222 | A | 7/1996 | Younes |
| 5,704,345 | A | 1/1998 | Berthon-Jones |

(Continued)

FOREIGN PATENT DOCUMENTS

| | | |
|---|---|---|
| EP | 0459647 | 12/1991 |
| EP | 0425092 | 8/1995 |

(Continued)

OTHER PUBLICATIONS

International Search Report and Written Opinion for Application No. PCT/AU2005/000006 dated Mar. 11, 2005.

*Primary Examiner* — Steven Douglas
(74) *Attorney, Agent, or Firm* — Lerner, David, Littenberg, Krumholz & Mentlik, LLP

(57) ABSTRACT

A method of operating a CPAP apparatus in which the interface pressure is controlled to rapidly drop at the start of expiration by an expiratory relief pressure (ERP) that is independent of instantaneous respiratory flow, following which the pressure rises to an inspiratory level at or shortly before the end of expiration, or at the onset of an expiratory pause, if any. The ERP is an increasing function of the inspiratory pressure. The expiratory pressure follows a template that is a function of the expected expiration time, the magnitude of the template being equal to the ERP. The current estimated proportion of expiration is determined by comparing the expiration time of the breath in progress to low-pass filtered expiratory durations measured for a number of the preceding breaths.

11 Claims, 2 Drawing Sheets

(56) References Cited

U.S. PATENT DOCUMENTS

| | | |
|---|---|---|
| 5,845,636 A | 12/1998 | Gruenke |
| 5,865,173 A | 2/1999 | Froehlich |
| 5,884,662 A | 3/1999 | Ko |
| 6,105,575 A | 8/2000 | Estes |
| 6,305,374 B1 | 10/2001 | Zdrojkowski et al. |
| 6,345,619 B1 | 2/2002 | Finn |
| 6,445,942 B1 | 9/2002 | Berthon-Jones et al. |
| 6,484,719 B1 | 11/2002 | Berthon-Jones |
| 6,532,957 B2 | 3/2003 | Berthon-Jones |
| 6,532,960 B1 | 3/2003 | Yurko |
| 6,553,992 B1 | 4/2003 | Berthon-Jones et al. |
| 6,575,163 B1 | 6/2003 | Berthon-Jones |
| 6,622,726 B1 | 9/2003 | Du |
| 6,626,176 B1 | 9/2003 | Madaus |
| 7,128,069 B2 | 10/2006 | Farrugia et al. |
| 7,866,318 B2 | 1/2011 | Bassin |
| 2004/0255943 A1 | 12/2004 | Morris |
| 2005/0005937 A1 | 1/2005 | Farrugia et al. |

FOREIGN PATENT DOCUMENTS

| | | |
|---|---|---|
| FR | 2850284 | 7/2004 |
| WO | 92/11054 | 7/1992 |
| WO | 98/12965 | 4/1998 |
| WO | 01/00267 | 1/2001 |
| WO | 2004/067070 | 8/2004 |
| WO | 2004/112680 | 12/2004 |
| WO | 02/02169 | 1/2011 |

US 8,899,231 B2

METHODS FOR PROVIDING EXPIRATORY PRESSURE RELIEF IN POSITIVE AIRWAY PRESSURE THERAPY

This application is a continuation of U.S. application Ser. No. 10/596,813, filed Jul. 19, 2006, now U.S. Pat. No. 7,866,318 now allowed, which is a U.S. National Phase application of PCT Application No. PCT/AU05/00006 filed Jan. 7, 2005 which claims the priority of Australian provisional application No. AU 2004900046 filed on Jan. 7, 2004 which is incorporated by reference.

FIELD OF THE INVENTION

The invention relates to a method and apparatus for delivering a supply of air at positive pressure to a patient for treating sleep disordered breathing. In particular, the invention relates to a method and apparatus which provides a smooth, comfortable pressure versus time waveform that is synchronized to the patient's breathing.

BACKGROUND OF THE INVENTION

Since the invention of nasal Continuous Positive Airway Pressure (nasal CPAP) for treatment of Obstructive Sleep Apnea (OSA) and other forms of Sleep Disordered Breathing (SDB) by Sullivan, as taught in U.S. Pat. No. 4,944,310, much effort has been directed towards improving the comfort of the devices. One aspect of this is a more comfortable patient interface, such as provided by the MIRAGE® and ULTRA MIRAGE® masks manufactured by ResMed Limited. Another aspect of providing a more comfortable patient interface is the comfort of the waveform of air at positive pressure provided by the blower.

Some low cost CPAP blower devices, such as the S7™ device by ResMed Limited, provide a supply of air at a generally fixed positive pressure throughout the respiratory cycle of the patient, for example, 15 cmH$_2$O. A blower comprising an electric motor and fan can be constructed to deliver air based on a rotational speed of the motor predetermined to deliver a particular pressure to a patient interface, such as a mask. When the patient breathes in with such a system, the pressure in the mask may reduce by a small amount. When the patient breathes out with such a system, the pressure in the mask may increase by a small amount. These fluctuations in mask pressure are referred to as "swing". Other blowers use feedback in a pressure controller which counterbalances the effect of patient effort on the mask pressure to reduce the swing.

Another group of CPAP devices, such as the ResMed AUTOSET® SPIRIT™ device can monitor the patient and determine an appropriate CPAP setting to deliver to the patient, which pressure may vary through the night, for example, delivering 15 cmH$_2$O during an initial portion of the patient's sleep, but increasing to 20 cmH$_2$O later in the night. Changes in pressure are made in response to a determination of the occurrence and severity of aspects of breathing such as flow limitation and snoring.

A bi-level CPAP device, such as the ResMed VPAP® product, provides a higher pressure to the patient's mask during the inspiratory portion of the respiratory cycle, for example, 10-20 cmH$_2$O, and a lower pressure during the expiratory portion of the patient's breathing cycle, for example, 4-10 cmH$_2$O. When the device makes a transition from the higher pressure to the lower pressure the motor is braked. When the device makes the transition from the lower pressure to the higher pressure, the motor is accelerated. A mismatch between the device control cycle and the patient respiratory cycle can lead to patient discomfort.

U.S. Pat. No. 6,345,619 (Finn) describes a CPAP device that provides air at a pressure intermediate the IPAP (Inspiratory Positive Airway Pressure) and EPAP (Expiratory Positive Airway Pressure) pressures during the transition between the inspiratory and expiratory portions of the device control cycle. U.S. Pat. No. 6,484,719 (Berthon-Jones) and U.S. Pat. No. 6,532,957 (Berthon-Jones) describe devices which provide pressure support in accordance with a waveform template. U.S. Pat. No. 6,553,992 (Berthon-Jones et al.) describes a ventilator whose servo-controller adjusts the degree of support by adjusting the profile of the pressure waveform as well as the pressure modulation amplitude. As the servo-controller increases the degree of support by increasing the pressure modulation amplitude, it also generates a progressively more square, and therefore efficient, pressure waveform; when the servo-controller decreases the degree of support by decreasing the pressure modulation amplitude, it also generates a progressively more smooth and therefore comfortable pressure waveform. The contents of all of these patents are hereby incorporated by reference.

CPAP and VPAP devices are mechanical ventilators. Ventilators have been classified (Chatburn, Principles and Practice of Mechanical Ventilation, Edited by M J Tobin, McGraw Hill, 1994, Ch. 2) as being either pressure, volume or flow controllers. In each case, the ventilator controls the pressure of air versus time, volume of air versus time, or flow of air versus time that is delivered to the patient. Many such devices can be programmed to deliver a variety of waveforms, such as pulse (rectangular), exponential, ramp and sinusoidal. The shape of the waveform actually delivered to the patient may be affected by the compliance and resistance of the patient's respiratory system and his breathing effort, as well as mechanical constraints such as blower momentum and propagation delays.

Ventilators have been constructed to deliver an inspiratory waveform when one of pressure, volume, flow or time reaches a preset value. The variable of interest is considered an initiating or trigger variable. Time and pressure triggers are common. The Puritan Bennett 7200a ventilator is flow triggered. The Drager Babylog ventilator is volume triggered. The Infrasonics Star Sync module allows triggering of the Infant Star ventilator by chest wall movement. The ventilator's inspiration cycle ends because some variable has reached a preset value. The variable that is measured and used to terminate inspiration is called the cycle variable. Time and volume cycled ventilators are known.

Many ventilators provide a Positive End-Expiratory Pressure (PEEP). Some of these ventilators use a valve (the PEEP valve) which allows the PEEP to be varied. Some devices, such as that taught by Ernst et al. in U.S. Pat. No. 3,961,627, provide a combination of pressure and flow control within one respiration cycle. A control cycle is divided into four phases I, II, III and IV. The respiration cycle and the control cycle do not necessarily have to fall together in time; mostly, however, phases I and II of the control cycle correspond to inspiration, and phases III and IV of the control cycle correspond to expiration. Phases I, III and IV are pressure-regulated, and phase II is flow-regulated. The doctor can choose the pressure course with the three control elements for the expiratory pressure decrease, the inflexion, and the final expiratory pressure. In phase III, the pressure proceeds from the pressure measured at the end of phase II according to a fixed pressure decrease dP/dt. When the pressure measured in phase III reaches the inflexion, the pressure proceeds linearly to the fixed final expiratory pressure. The part of the expiration from the inflexion to the end of the respiration cycle represents phase IV. The linear course of the pressure in the expiration represents a preferred embodiment, but could be replaced by another course of the pressure curve, for example, an exponential.

A spontaneously breathing patient exerts at least some effort to breath, however inadequate. A lack of synchrony between the respiratory cycle of the patient and that of the ventilator can lead to patient discomfort.

In Proportional Assist Ventilation (PAV), as described by Magdy Younes, the ventilator generates pressure in proportion to patient effort; the more the patient pulls, the higher the pressure generated by the machine. The ventilator simply amplifies patient effort without imposing any ventilatory or pressure targets. It is understood that the objective of PAV is to allow the patient to comfortably attain whatever ventilation and breathing pattern his or her control system sees fit. The PAV system is further discussed in U.S. Pat. Nos. 5,044,362, 5,107,830, 5,540,222 and 5,884,662.

U.S. Pat. No. 5,535,738 (Estes et al.) describes a further PAV apparatus.

Another technique for improving patient comfort is disclosed in copending U.S. application Ser. No. 10/871,970 in the name of Farrugia et al. filed on Jun. 18, 2004. In this method, upon detection of the transition from inspiration to expiration, the blower motor is allowed to freewheel.

Despite the many approaches that have been taken to improve patient comfort, patients receiving CPAP therapy frequently complain of difficulty in exhaling, particularly at higher CPAP pressures. The work of breathing is increased by CPAP. The expiratory reserve volume during CPAP is higher than when CPAP is not present, which is unpleasant for many patients. Subjectively it is hard to breathe out, though easy to breathe in. Bilevel ventilation does not necessarily alleviate these problems. In bilevel ventilation, there are typically delays in detecting the onset of inspiration and then in delivering the desired increase in pressure to the inspiratory level. Suppose, for example, that a certain mask pressure is necessary to prevent upper airway obstruction at peak inspiratory flow, and the bilevel inspiratory positive airway pressure (IPAP) is set to equal this pressure. Then because of the above-mentioned delays, it may be the case that the pressure delivered is less than IPAP at the time of peak inspiratory flow, resulting in upper airway obstruction. More generally, the pressure required to prevent upper airway obstruction varies during the respiratory cycle, and the delay in delivering IPAP may result in a pressure below that required to prevent obstruction, more probably earlier in inspiration than at the time of peak inspiratory flow, when the difference between the actual pressure and that required to prevent obstruction is larger.

In order to prevent this, it may be necessary to set IPAP to a level somewhat above the pressure required to prevent obstruction at peak inspiratory flow (which is probably the optimum level), and it is not easy to determine how high this pressure should be. In particular, a reasonably optimal IPAP cannot be easily determined from the results of a previous CPAP titration. Of course, setting the bilevel expiratory positive airway pressure (EPAP) to the CPAP level determined from a previous titration will prevent obstruction, but will yield an IPAP significantly above that CPAP level. Under these circumstances, the bilevel ventilator will perform some of the work of breathing, but deliver pressures significantly above those actually required.

There is a need for an improved method that provides expiratory pressure relief, removes the possibility of runaway pressure falls during expiration, and ensures that the pressure during inspiration is sufficient to prevent airway collapse, with the parameters determining the pressure level (if not set automatically) being based on the results of a previous CPAP titration.

BRIEF SUMMARY OF THE INVENTION

In the invention, there is provided a CPAP apparatus that provides air at a first positive pressure during an inspiratory portion of a control cycle of the apparatus and air at a second positive pressure during an expiratory portion of a control cycle of the apparatus, and a smoothly varying pressure waveform between the inspiratory and expiratory portions of the control cycle.

During inspiration, the pressure remains at the IPAP level. When expiration is detected, the pressure is lowered rapidly, by an amount (the "expiratory relief pressure" (ERP)) that is either fixed or determined by an automatic method, but in any case by an amount that is not dependent on instantaneous respiratory flow. The pressure is then raised typically more slowly during the remainder of expiration, in a manner intended to cause the pressure to reach the determined inspiratory level at or shortly before the end of expiration, or at the onset of the expiratory pause, if any.

During expiration, the pressure drops rapidly by an amount equal to the ERP, and it then increases towards the IPAP level so that the pressure is at the IPAP level at the start of inspiration. The expiratory pressure thus decreases and then increases during expiration. It follows a waveform or template that is a function of the expected expiration time, the magnitude of the waveform or template being equal to the ERP. The desired instantaneous pressure during expiration can be determined by calculating the current estimated proportion of expiration. To determine the current estimated proportion of expiration it is necessary to know the expected expiration duration, and various methods are described for calculating this.

DETAILED DESCRIPTION OF THE INVENTION

Figure 1:
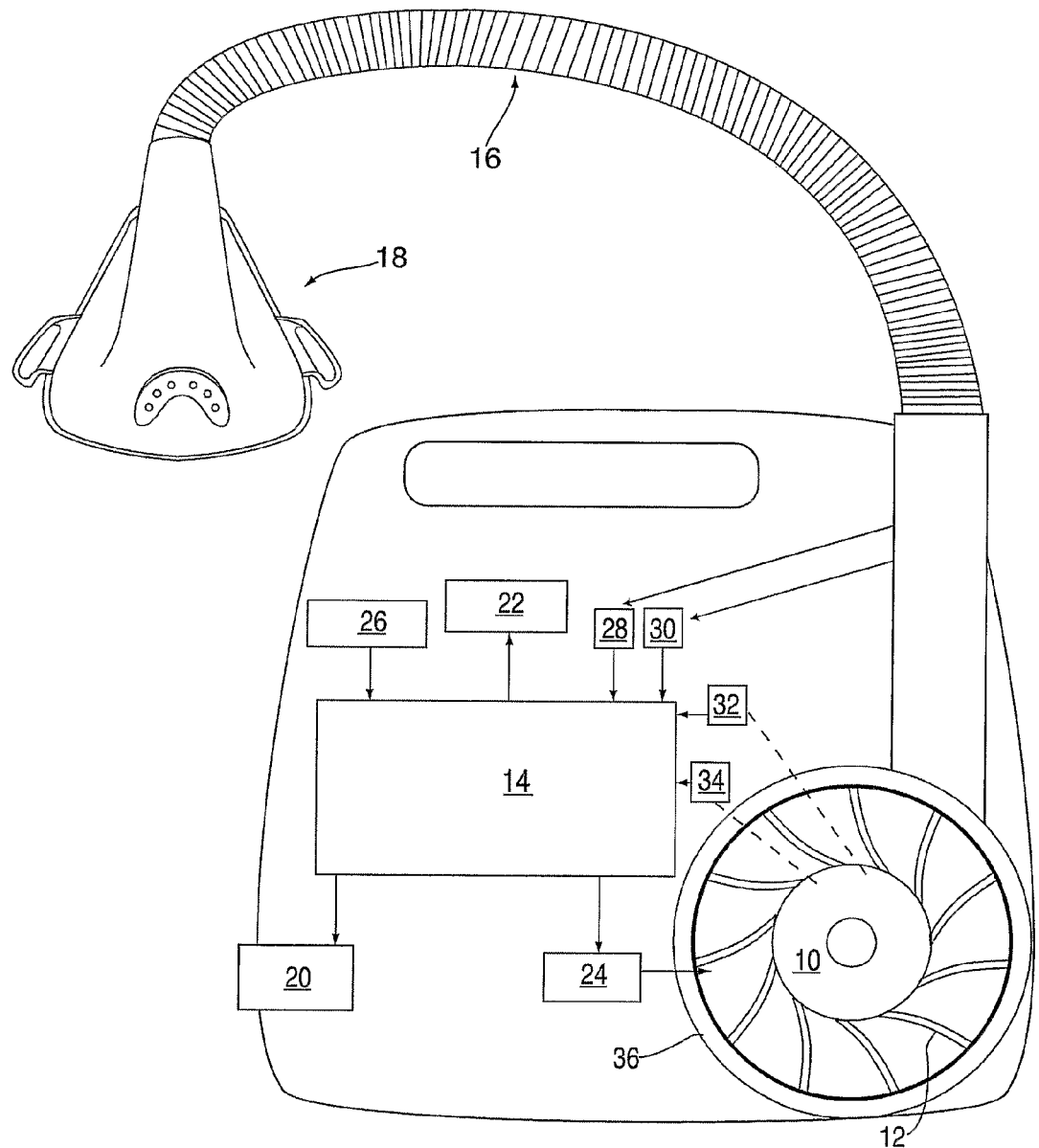
FIG. 1 shows a CPAP apparatus in accordance with an embodiment of the invention.

FIG. 1 shows apparatus in accordance with an embodiment of my invention. An electric motor 10 has an impeller 12 attached to it. The impeller 12 resides in a volute 36. The motor 10 is under the control of a motor controller 24 (suitable controllers include TMS320LC2402 or MC33035 IC). The motor includes sensors 32, 34 that provide signals indicative of motor rotational speed and current respectively. When the windings of the motor are energized, the impeller rotates. Air is drawn in through the inlet of the impeller and gains momentum. As the air passes out of the impeller and into the volute, it changes speed and develops pressure. Air passes out of the volute, past flow and pressure sensors 28, 30 (such as SM15652-003 flow sensor and SM15652-008 or MPX2010 pressure sensors) respectively to an air delivery conduit 16 (for example, manufactured by Smooth-bor Plastics) that is in turn connected to a patient interface 18 which in the illustrated embodiment is a nasal mask, for example, a MIRAGE® or ULTRA MIRAGE® mask manufactured by ResMed Limited. Other forms of patient interface may be used, for example, a full-face mask, nasal prongs and nasal cushions.

The flow and pressure sensors 28, 30 provide data to a microcontroller 14. Suitable microcontrollers include the HITACHI SH 7032/34 which are 32-bit RISC devices, with a clock rate of 2-20 MHz, 8 or 10 bit A-D converters and a variety of Input and Output features. The microcontroller 14 uses the Nucleus Plus Real-time Operating System (RTOS) by Accelerated Technologies Incorporated. The apparatus can deliver a predetermined CPAP pressure such as is delivered by the S7 ELITE by ResMed Limited. The microcontroller 14 can also be programmed to deliver CPAP therapy in accordance with U.S. Pat. No. 5,704,345 (Berthon-Jones) which teaches a method and apparatus for detection of apnea and obstruction of the airway in the respiratory system. The contents of U.S. Pat. No. 5,704,345 are hereby incorporated by cross-reference.

The microcontroller 14 is programmed to detect the patient's transition between the inspiratory and expiratory portions of the patient's respiratory cycle. There are a number of ways of accomplishing this detection. One way is to monitor the flow of air to and from the patient. When the respiratory flow signal crosses zero (a "zero-crossing") there has been a transition between inspiration and expiration. Alternatively or additionally, the mask pressure may be monitored. When mask pressure falls below a first pressure threshold, inhalation is taken to have occurred. When mask pressure rises above a second threshold, exhalation is taken to have occurred. Alternatively or additionally, an effort sensor may be used on the patient, for example, to determine chest wall movements, movement of the supra-sternal notch or other patient movements (for example, as described in U.S. Pat. No. 6,445,942). Measurement techniques may be combined with timed estimates of the period of a breath. For example, an average breath rate of the patient may be measured and when inhalation is detected by a flow, pressure or effort sensor, exhalation is assumed to occur after a period based on the measured average breath rate. (This general technique is discussed in the above-identified copending U.S. application Ser. No. 10/871,970 in the name of Farrugia et al. filed on Jun. 18, 2004.)

The apparatus includes a display 22, for example, a 2 line by 16 character LCD or similar display device. The apparatus includes a keypad 26, such as one using backlit silicone switches. The device also includes a power supply which provides 40W at 24V with Class II isolation manufactured by SKYNET. The apparatus may include an interface 20 to enable communication with external devices. For example, a suitable interface chip is the MAX3130/MAX3131 from MAXIM. These chips provide both IrDA and RS-232 communication.

A CPAP device such as the S7 ELITE manufactured by ResMed Limited may be adapted to incorporate my invention. Generally, the controller of the CPAP apparatus according to an embodiment of my invention is programmed to deliver a CPAP pressure in the range of 4 to 25 cm H$_2$O. In an automatically adjusting form of the apparatus, such as the AutoSet SPIRIT and as taught in the above-mentioned U.S. Pat. No. 5,704,345, the CPAP apparatus is programmed to increase the CPAP pressure to overcome or prevent partial or complete obstructions of the airway as indicated by the presence of snoring, apneas or flow flattening. Upon detection of an apnea, the pressure may remain at the higher level during both inhalation and exhalation. In addition, upon the detection of cessation of the apnea (i.e., resumption of normal breathing) or expiration of a preset period of time, the reduction of pressure during exhalation mode may be resumed.

The controller 14 is programmed to reduce the pressure of air in the patient interface delivered to the patient during the exhalation portion of the respiratory cycle of the patient from the treatment pressure recommended by the patient's physician. For each breath, an inspiratory pressure is determined, being either a fixed value set by a clinician or a value calculated by an automatic method such as an AutoCPAP algorithm, e.g., the ResMed AUTOSET® algorithm (see, for example, WO 98/12965 or U.S. Pat. No. 6,575,163). During inspiration, the pressure remains at this level (IPAP). When expiration is detected, the pressure is lowered rapidly, by an amount (the "expiratory relief pressure" (ERP)) that is either fixed or determined by an automatic method, but in any case by an amount not dependent on instantaneous respiratory flow. Pressure is then raised typically more slowly during the remainder of expiration, in a manner intended to cause the pressure to reach the determined inspiratory level at or shortly before the end of expiration, or at the onset of the expiratory pause, if any.

The ERP may be determined automatically as a function of the IPAP, which is an increasing function (but not necessarily strictly increasing), for example, $$P_{ERP}(P_{IPAP}) = \begin{cases} 0 & \text{if } P_{IPAP} \leq 4 \\ \frac{(P_{IPAP}-4)}{12-4} P_{ERP,max}, & \text{if } 4 < P_{IPAP} < 12 \\ P_{ERP,max} & \text{otherwise} \end{cases}$$

where the units of pressure are cm H$_2$O, and a typical value of $P_{ERP,max}$ might be 3 cm H$_2$O. The notation $P_{ERP}$ ($P_{IPAP}$) means that the expiratory relief pressure $P_{ERP}$ is a function of the IPAP level. If the IPAP level is low (equal to or less than 4 cmH$_2$O), then the expiratory relief pressure ERP is zero—the IPAP and EPAP levels are the same and there is no bilevel operation, just a constant CPAP pressure. If the IPAP level is very high (greater than 12 cmH$_2$O), then the expiratory relief pressure is not allowed to exceed a maximum value, $P_{ERP,max}$. At IPAP levels between the two extremes, the expiratory relief pressure $P_{ERP}$ varies with the IPAP level, the formula being such that the values at the two extremes are 0 and $P_{ERP,max}$ respectively.

One reason to keep the ERP low at low IPAP is to keep expiratory pressure high enough to ensure adequate mask vent flow. (Since EPAP is equal to IPAP minus ERP, EPAP decreases with IPAP.) Another is that less expiratory pressure relief is required at lower pressures because the additional work of breathing presented by the CPAP is less.

Figure 2:
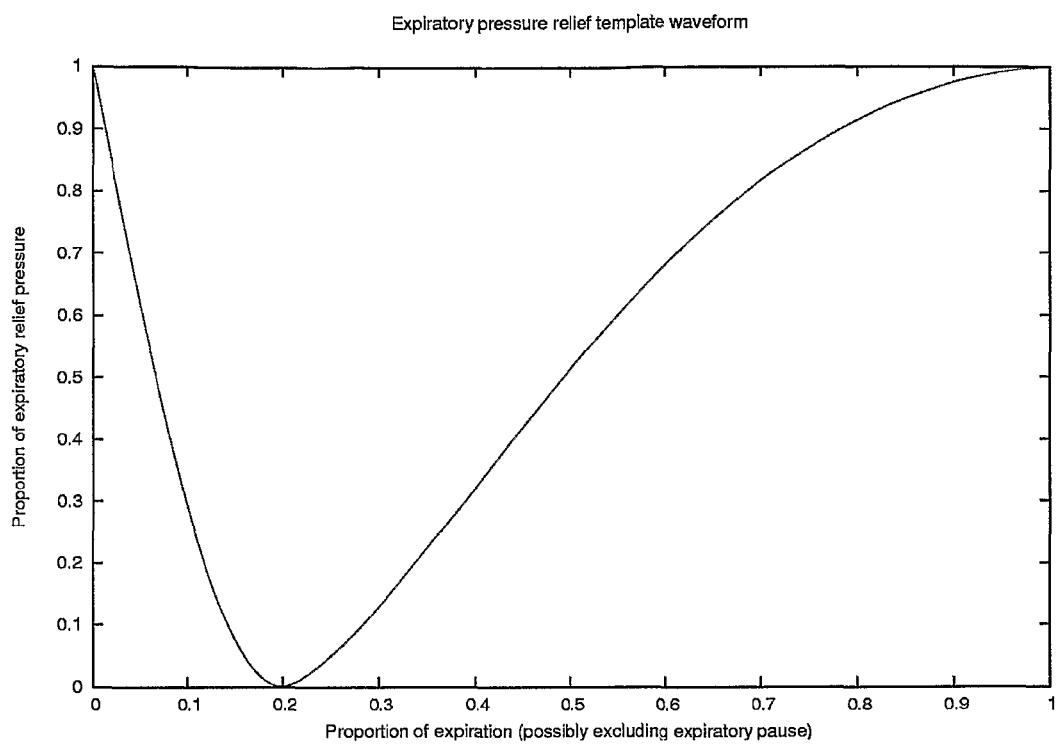
FIG. 2 shows a function R that is used in calculating the instantaneous pressure during expiration by determining the current estimated proportion of expiration and calculating from this the proportion of expiratory relief pressure to be delivered.

The ERP is the difference between the IPAP and EPAP values, but this does not mean that only two pressure values are used. IPAP is constant during inspiration. During expiration, the pressure drops rapidly by an amount equal to the ERP, and it then increases towards the IPAP level so that the pressure is at the IPAP level at the start of inspiration. The expiratory pressure thus decreases and then increases during expiration. It follows a waveform or template that is a function of the expected expiration time, the magnitude of the waveform or template being equal to the ERP. One method of calculating the instantaneous pressure during expiration is by determining the current estimated proportion of expiration and calculating from this the proportion of expiratory relief pressure to be delivered, using a function R whose general appearance is shown in FIG. 2. In this form of the invention, the instantaneous pressure delivered during expiration is $$P = P_{IPAP} - P_{ERP} \cdot R(\alpha)$$

where α is the current estimated proportion of expiration. In this case, the variable a extends throughout expiration (from 0 to 1.0), including the expiratory pause.

In another form of the invention the instantaneous pressure delivered during expiration is $$P = \begin{cases} P_{IPAP} - P_{ERP}R(\beta) & \text{before the expiratory pause} \\ P_{IPAP} & \text{during the expiratory pause} \end{cases}$$

where β is the current estimated proportion of the non-expiratory-pause part of the breath. Referring to FIG. 2, the variable β also extends from 0 to 1.0, but the limit 1.0 corresponds to the start of the expiratory pause. In other words, the template for the expiratory pressure is the same as that for the first case, but it is 'squeezed' into less of the expiration time. The pressure during the expiratory pause is equal to IPAP.

In both forms of the invention, it is necessary to estimate a proportion of expiration, either a proportion a of the entire expiratory cycle or a proportion β of the expiratory cycle prior to the expiratory pause. There are several methods for doing this.

Method 1—Estimating Proportion of Expiration (α):

This method is based on estimated respiratory flow, for example, such as is commonly used in ventilators, and is used to determine the start of inspiration and the start of expiration. From this information the duration of expiration $T_{exp}$ can be calculated. Low-pass filtering a time series of expiratory durations yields a typical expiratory duration $T_{exp,LPF}$. One form of low-pass filter which may be used is the discrete-time first-order IIR filter with the filter update for breath number m being $$T_{exp,LPF,m} = kT_{exp,m} + (1-k)T_{exp,LPF,m-1}$$

where typical values of k are between 0.1 and 0.2. In this equation, $T_{exp,LPF,m}$ is the filter update (the expiratory duration to be used for the next breath) taking into account the expiratory duration $T_{exp,m}$ measured for the current breath m, and $T_{exp,LPF,m-1}$ is the previous filter update calculated for the preceding breath.

An alternative is a median filter with a length of preferably between 5 and 7 elements, which has the advantage of rejecting outliers better than a linear low-pass filter.

The estimated current proportion of expiration is then calculated from the current time into expiration $t_{exp}$ by $$\alpha = \frac{t_{exp}}{T_{exp,LPF}}.$$

Method 2—Estimating Proportion of Non-Expiratory Part of Expiration (β):

This method first requires that a determination be made of when the expiratory pause starts. The expiratory pause may be considered to start when the estimated flow during expiration first exceeds a small negative value such as −0.07 l/sec. (Throughout this disclosure, expiratory flow is taken to be negative.) It is desirable to perform this calculation using low-pass-filtered flow with a low −3 dB point, such as 5 Hz, in order better to reject artefacts. Allowance needs to be made for the delay caused by such a filter. Since the analysis can be retrospective for each breath, in which case the entire expiratory flow waveform and part of the inspiratory flow waveforms before and after it are available, a time-symmetrical FIR filter (or the equivalent of delaying the waveform used for determination of the start of expiration by the same amount) may be used to avoid a delay between the two signals.

Another way to determine when the expiratory pause starts is to examine the entire expiratory waveform, possibly low-pass-filtered as in the preceding technique, starting from the end of expiration and proceeding back in time. The expiratory pause is the longest contiguous period ending at the end of expiration such that the respiratory flow during that period does not lie outside a range of values which represents "small" flow, e.g., the interval −0.07 to +0.07 l/sec. The flow may be small positive and yet be part of the expiratory pause most notably because of cardiogenic airflow, or because of other artefacts not related to respiratory effort.

Once it is determined when the expiratory pause is expected to start, it is possible to determine a typical non-pause-expiration duration $T_{exp,np,LPF}$. As in method 1 for determining a above, the estimated respiratory flow can be used to determine the start of expiration. The duration of non-pause-expiration (i.e., non-expiratory-pause part of expiration) $T_{exp,np}$ is simply the difference between the time of the start of the expiratory pause and the time of the start of that expiration cycle. As in the determination of typical expiratory duration above, low-pass filtering a time series of non-pause-expiration durations yields a typical non-pause-expiration duration $T_{exp,np,LPF}$.

Another way to determine a typical non-pause-expiration duration $T_{exp,np,LPF}$ is to employ fuzzy logic (see, for example, U.S. Pat. No. 6,484,719). The membership function for the fuzzy logical quantity "small flow" is 0 for absolute values of respiratory flow greater than a value such as 0.15 l/sec and is 1 for absolute values of flow less than a smaller value such as 0.05 l/sec, with linearly interpolated values in between. The "expiratory pause" fuzzy quantity is the fuzzy AND of "small flow" and $T_{exp} > 0.2$ sec (because small negative flows should be ignored in early expiration, these cannot be part of the expiratory pause). The expiratory pause fraction $F_{exp,p,LPF}$ is the low-pass-filtered value of the "expiratory pause" fuzzy logical quantity, where this filter is updated only during expiration and has a time constant of 16 seconds. The quantity $T_{exp,LPF}$ is calculated as described above in method 1. Once $T_{exp,LPF}$ and $F_{exp,p,LPF}$ are known, the quantity of interest can be calculated:

$$T_{exp,np,LPF}(1 - F_{exp,p,LPF})T_{exp,LPF}$$

Because this is a fuzzy method, the flow need not be as vigorously low-pass-filtered as in the first method in order to perform satisfactorily when there are artefacts in the flow signal. It is now possible to determine β. During expiration, let time since the beginning of expiration be $t_{exp}$. Then if $$t_{exp} \geq T_{exp,np,LPF}$$

the breath is in expiratory pause; otherwise $$\beta = \frac{t_{exp}}{T_{exp,np,LPF}}.$$

The methods described above are based on the time into the current expiration (either taking into account the expiratory pause or not) and do not instantaneously depend on the current respiratory flow, except that respiratory flow is used to detect the start of inspiration. When breaths are typical (i.e., the last several breaths are alike) this method works well, particularly if the expiratory pause method is used and there is an expiratory pause, because if an expiration is shorter than usual, this often occurs at the expense of the expiratory pause, and the pressure (in an ideal mechanical implementation) has already reached IPAP by the start of the expiratory pause. However, on occasion an atypically short expiration may result in the pressure being well under IPAP by the end of the breath. (In other words, the pressure has not returned back up to the IPAP value.) In order to prevent this, an additional overriding algorithm may be used to deal with atypically short expirations. In this method, if the flow during expiration reaches a small negative threshold value such as −0.15 l/sec when the calculated α or β is such that a more negative value of flow was expected, e.g., if β<0.6, then the pressure is ramped rapidly up to IPAP, for example, over a time of 0.2 $T_{exp,np,LPF}$.

Method 3—Estimating Proportion of Expiration (α) and Proportion of Non-Expiratory-Pause Part of Expiration (β):

In commonly owned U.S. Pat. No. 6,484,719, a method using fuzzy logic is described for the determination of respiratory phase φ. The angles associated with the expiratory fuzzy logical rules given in the table in column 21 of that patent are dependent on a factor k. In that patent, k is the ratio of the standard inspiratory to the standard expiratory times. In the preferred implementation in this patent, k is an estimate of the proportion of time during expiration which is not the expiratory pause; using the definitions give above, it could be calculated by $$k = \frac{T_{exp,np,LPF}}{T_{exp,LPF}}.$$

In the preferred implementation, $$k=1-F_{exp\,pause}$$

where the expiratory pause fraction $F_{exp\,pause}$ is the low-pass-filtered value of the fuzzy logical quantity EXP PAUSE, the filter having the property that it is updated only during expiration. For example, if EXP PAUSE is 1 during 0.25 of expiration and 0 during the rest of expiration, the mean value of $F_{exp\,pause}$ is 0.25. If EXP PAUSE is 1 during 0.1 of expiration, 0.5 during 0.3 of expiration, and 0 during the rest of expiration, its mean value is also 0.25. In the preferred implementation, the expiratory pause fraction low-pass filter is a first order low-pass filter with a time constant of 4 times the long-term average of the respiratory period.

More fuzzy logical rules may be added to those described in U.S. Pat. No. 6,484,719 to provide smoother and more reliable phase detection. In particular, the preferred implementation contains two additional expiratory rules:

EARLY MID EXP=flow is decreasing AND flow is large negative

LATE MID EXP=flow is increasing AND flow is large negative

The angles associated with these rules are adjusted during algorithm refinement (but not during operation of the invention), by iteratively increasing or decreasing them, in order to give a rate of change of phase during expiration as nearly constant as possible.

It will be appreciated that these modifications of U.S. Pat. No. 6,484,719 are useful for the purposes contemplated in that patent as well as the purposes contemplated in the present patent.

Given φ as calculated by the fuzzy phase algorithm, it is straightforward to calculate $$\beta_P = \frac{2(\phi - 0.5) - F_{exp\,pause}}{1 - F_{exp\,pause}}.$$

Then, if $\beta_P<0$, the patient is in inspiration, if $\beta_P \geq 1$, the patient is in the expiratory pause, else $$\beta=\beta_P.$$

Another way of looking at the combination of this method of calculating β and the method for determining desired pressure based on β given above is that it is equivalent to the method described in U.S. Pat. No. 6,484,719 with a different template pressure function Π(φ), namely, a function which is 1 for inspiratory phase, and of the general form of the expiratory pressure relief waveform given above for expiratory phase, with the minor change being that the template does not determine pressure during the expiratory pause, but a quantity equal to $$\Pi\left(0.5 + \frac{\beta}{2}\right)$$

is used in the calculation of pressure during the non-expiratory pause part of expiration, and the value 1 is used for Π during the expiratory pause.

The fuzzy phase rules in U.S. Pat. No. 6,484,719 depend on a target ventilation. This target ventilation is calculated as the low-pass-filtered observed ventilation, using a first-order filter with a time constant on the order of 1 minute, though longer and shorter time constants work reasonably well. The system is initialised with a target ventilation of 3 l/min to ensure that it is not overly prescriptive initially. Since the system described in that patent was intended to deal with hypopnoea by delivering pressure support in a prescriptive manner, tending to ignore the patient to the extent that the patient was apnoeic, and the current invention has no such requirement, the rules can be modified in an obvious way to diminish or remove altogether their dependence on hypopnoea or hyperpnoea.

In this method for determining β, pressure depends on instantaneous flow because breath phase depends on instantaneous flow, and is capable of responding appropriately to unusually short expiratory times. Hence the method discussed above for dealing with atypical breaths, intended for situations where instantaneously β depends only on time into the current expiration, is here neither necessary nor appropriate.

Particularly in less expensive mechanical systems for the delivery of pressure, there may be marked delays between a pressure being requested by a control system and that pressure being delivered, due, for example, to relatively high moments of inertia of the motor and fan. After the initial detection of expiration, and provided the fuzzy phase determination system is not being used, the requested pressure is only a function of time (except for the system used to deal with atypical breaths described above). Hence the desired pressure in the near future is known, and so it is possible to compensate for an expected delay by requesting pressures in advance by an amount equal to the expected delay. This is an advantage of the present invention over systems which respond to instantaneous flow.

Although the invention has been described with reference to particular embodiments, it is to be understood that these embodiments are merely illustrative of the application of the principles of the invention. Numerous modifications may be made therein and other arrangements may be devised without departing from the spirit and scope of the invention.

I claim:

1. A method of determining the expiratory proportion of a breath, p, comprising the steps of:
    monitoring a respiratory flow of air of a patient;
    calculating an expected duration of expiration, d, from at least one prior breath from said respiratory flow;
    determining the start of exhalation of the patient within the breath;
    calculating a time, t, since the start of exhalation of the patient; and
    calculating p from the ratio of t and d.

2. A method in accordance with claim 1 wherein the expected duration of a breath is calculated by low pass filtering a time series of prior expiratory durations.

3. A method in accordance with claim 2 wherein the low pass filter is an Infinite Impulse Response (IIR) filter.

4. A method in accordance with claim 3 wherein the IIR filter is first-order.

5. A method in accordance with claim 1 wherein the expected expiratory duration, $d_{m+1}$, of the (m+1)th breath is calculated from the duration of the current breath $d_m$, the previous breath $d_{m-1}$ and a constant k in accordance with the following equation:

$$d_{m+1} = k\, d_m + (1-k) d_{m-1}.$$

6. A method in accordance with claim 2, wherein a low pass filter update $T_{exp,LPF,m}$, being the expected expiratory duration to be used for the next breath, is calculated by the following equation:

$$T_{exp,LPF,m} = kT_{exp,m} + (1-k)T_{exp,LPF,m-1}$$

where k is a constant, $T_{exp,m}$ is the expiratory duration measured for the current breath m, and $T_{exp,LPF,m-1}$ is the previous filter update calculated for the preceding breath.

7. A method in accordance with claim 5 wherein the constant k is generally in the range of 0.1 to 0.2.

8. A method in accordance with claim 1 wherein the expected duration of a breath is calculated using a median filter.

9. A method in accordance with claim 8 wherein the median filter has a length in the range of 5 to 7 elements.

10. A method in accordance with claim 3, wherein a low pass filter update $T_{exp,LPF,m}$, being the expected expiratory duration to be used for the next breath, is calculated by the following equation:

$$T_{exp,LPF,m} = kT_{exp,m} + (1-k)T_{exp,LPF,m-1}$$

where k is a constant, $T_{exp,m}$ is the expiratory duration measured for the current breath m, and $T_{exp,LPF,m-1}$ is the previous filter update calculated for the preceding breath.

11. A method in accordance with claim 6 wherein the constant k is generally in the range of 0.1 to 0.2.

* * * * *